(12) United States Patent
Hwang et al.

(10) Patent No.: US 11,865,521 B2
(45) Date of Patent: Jan. 9, 2024

(54) BIFUNCTIONAL CATALYST FOR HYDROGENATION OF CARBON DIOXIDE, AND METHOD FOR PREPARING HYDROCARBON BY USING SAME

(71) Applicant: KOREA RESEARCH INSTITUTE OF CHEMICAL TECHNOLOGY, Daejeon (KR)

(72) Inventors: Sun Mi Hwang, Daejeon (KR); Ki Won Jun, Daejeon (KR); Seok Ki Kim, Daejeon (KR); Hae Gu Park, Daejeon (KR); Seung Ju Han, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 264 days.

(21) Appl. No.: 17/424,857

(22) PCT Filed: Jan. 23, 2020

(86) PCT No.: PCT/KR2020/001153
§ 371 (c)(1),
(2) Date: Jul. 21, 2021

(87) PCT Pub. No.: WO2020/153780
PCT Pub. Date: Jul. 30, 2020

(65) Prior Publication Data
US 2022/0088578 A1    Mar. 24, 2022

(30) Foreign Application Priority Data

Jan. 23, 2019 (KR) .................. 10-2019-0008697

(51) Int. Cl.
*B01J 23/745* (2006.01)
*B01J 21/18* (2006.01)
*B01J 37/04* (2006.01)
*B01J 37/06* (2006.01)
*B01J 37/08* (2006.01)
*C07C 1/04* (2006.01)

(52) U.S. Cl.
CPC ............. *B01J 23/745* (2013.01); *B01J 21/18* (2013.01); *B01J 37/04* (2013.01); *B01J 37/06* (2013.01); *B01J 37/08* (2013.01); *C07C 1/044* (2013.01); *C07C 2521/18* (2013.01); *C07C 2523/745* (2013.01)

(58) Field of Classification Search
CPC . B01J 23/745; B01J 21/18; B01J 37/04; B01J 37/06; B01J 37/08; C07C 1/044; C07C 2521/18; C07C 2523/745
USPC .................. 502/338; 518/713, 715, 719, 721
See application file for complete search history.

(56) References Cited

U.S. PATENT DOCUMENTS

| 2011/0105630 A1 | 5/2011 | Dorner et al. | |
| 2011/0143913 A1* | 6/2011 | Yang | ..................... H01M 4/925 |
| | | | 502/215 |
| 2014/0296357 A1* | 10/2014 | Ozaki | .................... B01J 35/006 |
| | | | 518/715 |

FOREIGN PATENT DOCUMENTS

| CN | 103721748 A | * | 4/2014 | ............. B01J 31/22 |
| CN | 113371693 A | * | 9/2021 | ........... C01B 32/158 |
| KR | 10-2014-0104636 A | | 8/2014 | |
| KR | 10-2014-0109224 A | | 9/2014 | |
| KR | 20140126099 A | * | 10/2014 | ............. B01J 21/18 |
| KR | 10-2016-0009125 A | | 1/2016 | |
| KR | 10-1644976 B1 | | 8/2016 | |
| KR | 10-1737484 B1 | | 5/2017 | |

OTHER PUBLICATIONS

International Search Report dated May 19, 2020 for corresponding international application No. PCT/KR2020/001153.
Written Opinion issued for corresponding International Patent Application No. PCT/KR2020/001153 dated May 19, 2020.

* cited by examiner

*Primary Examiner* — Patricia L. Hailey
(74) *Attorney, Agent, or Firm* — Hauptman Ham, LLP

(57) ABSTRACT

The present disclosure relates to a bifunctional catalyst for manufacturing a hydrocarbon from carbon dioxide and hydrogen. The bifunctional catalyst includes a carbon composite including cobalt (Co) and nitrogen (N) atoms forming a coordinate bond with the cobalt, and metal particles which exhibit a catalytic activity for a Fischer-Tropsch synthesis reaction and which are dispersed on the inner pore surface and/or the outer surface of the carbon composite support, thus simultaneously promoting a reverse water gas shift reaction and the Fischer-Tropsch synthesis reaction.

12 Claims, 5 Drawing Sheets

BIFUNCTIONAL CATALYST FOR HYDROGENATION OF CARBON DIOXIDE, AND METHOD FOR PREPARING HYDROCARBON BY USING SAME

CROSS-REFERENCE TO RELATED APPLICATION

The present application is a national stage filing under 35 U.S.C § 371 of PCT application number PCT/KR2020/001153 filed on Jan. 23, 2020 which is based upon and claims the benefit of priorities to Korean Patent Application No. 10-2019-0008697, filed on Jan. 23, 2019, in the Korean Intellectual Property Office. Both of the aforementioned applications are hereby incorporated by reference in their entireties.

TECHNICAL FIELD

The present disclosure relates to a catalyst for hydrogenation of carbon dioxide including a carbon composite support and a method of manufacturing a hydrocarbon from a reaction of carbon dioxide and hydrogen using the same. More particularly, the present disclosure relates to a bifunctional catalyst having two kinds of catalytic activities for both a reverse water gas shift reaction and a Fischer-Tropsch synthesis reaction to easily convert carbon dioxide into a hydrocarbon, and to a method of manufacturing a hydrocarbon using the same.

BACKGROUND ART

Coal and petroleum are fossil energy resources that account for more than 50% of the total energy resource that have been used as important energy sources for mankind for the past several centuries. Humans have been emitting thermodynamically stable carbon dioxide without a separate post-treatment process through these various energy conversion processes.

However, currently, as it is known that carbon dioxide is the main greenhouse gas that accounts for 55% of the contribution to global warming, various technologies of removing carbon dioxide have been proposed. Among them, technologies of hydrogenating carbon dioxide using a catalyst to convert carbon dioxide into high value-added chemical raw materials such as alpha olefins or liquid fuels such as gasoline or diesel are the most preferred because the technologies are easy to be technically linked with conventional industrial processes, a large market for products is secured, and it is possible to easily process a large amount of carbon dioxide.

Although the reaction mechanism for hydrogenating carbon dioxide to synthesize a hydrocarbon has not yet been clearly identified, it is generally known that a two-step continuous reaction is performed. Specifically, the hydrogenation of carbon dioxide includes a first step of converting carbon dioxide supplied as a reactant into carbon monoxide using a reverse water gas shift (RWGS) reaction, and a second step of bonding the generated carbon monoxide to hydrogen using a Fischer-Tropsch (FTS) reaction to perform conversion into a hydrocarbon. The reverse water gas shift reaction of the first step is an endothermic reaction and may be represented by the following Formula 1.

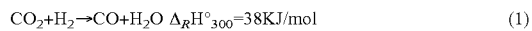
$$CO_2+H_2 \rightarrow CO+H_2O \ \Delta_R H°_{300}=38KJ/mol \quad (1)$$

The reverse water gas shift reaction of this first step is a reversible reaction, and the reverse reaction thereof (reaction of from CO and $H_2O$ to $CO_2$ and $H_2$) is known as a water gas shift reaction. The reverse water gas shift reaction may be performed under a condition providing partial conversion of $CO_2$ and $H_2$, thereby generating a total product mixture containing carbon monoxide (CO) and $H_2O$. Thereafter, the carbon monoxide generated in the first step is subjected to a Fischer-Tropsch synthesis (FTS) reaction in the second step. The FTS reaction is exothermic and may be represented by the following Formula 2.

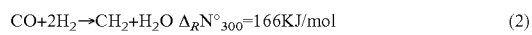
$$CO+2H_2 \rightarrow CH_2+H_2O \ \Delta_R N°_{300}=166KJ/mol \quad (2)$$

"$CH_2$" in Formula 2 above refers to a general hydrocarbon moiety that may be incorporated into larger molecules, for example, ethylene ($C_2H_4$) or propylene ($C_3H_6$).

Accordingly, as described above, $CO_2$ may be converted into CO through the RWGS reaction, and CO and $H_2$ may be then reacted with each other through the FT reaction, thus generating light olefins from $CO_2$.

One of the important factors in the Fischer-Tropsch synthesis reaction as described above is a catalyst. Among the catalysts, cobalt-based and iron-based catalysts are mainly used. In the case of the cobalt-based catalyst, the catalytic activity is favorable and the probability of carbon chain expansion is high, so there are merits in that the selectivity of long carbon chains to products is high and that the catalyst life is long. The iron-based catalyst is widely used as a catalyst for Fischer-Tropsch synthesis reaction because the iron-based catalyst is relatively inexpensive and has a wide selection of reactor operating conditions and because a proportion of useful products such as branched hydrocarbons and light olefins is high.

Meanwhile, a support as well as an active material is frequently used in the catalyst. This is for dispersing the active material on the support, thus increasing the surface area of the active material and improving stability.

A generally used support is present in the form of an oxide such as alumina ($Al_2O_3$) or silica ($SiO_2$), and the oxide support as described above is inexpensive, has a large specific surface area, and is relatively stable, thus being widely used as a catalyst support in a Fischer-Tropsch synthesis reaction and various reactions.

However, the oxide support as described above is easily bonded to an active material such as iron and cobalt, thereby reducing the performance of the catalyst. Further, the bonding material between the active material and the oxide support has no activity for a catalytic reaction and it is difficult to reduce the active material, which acts as a factor to shorten the life of the catalyst from a long-term perspective. Accordingly, there is a need for a catalyst support including a new economical material other than the oxide support as described above.

Korean Laid-Open Patent Application No. 10-2016-0123477 discloses a technology related to a catalyst for Fischer-Tropsch reaction in which carbon nitride having meso-sized pores is used as a catalyst support and an active material of an iron component is carried in the catalyst support, and a method of manufacturing the same. US Patent Application Publication No. 2011/0105630 discloses a catalyst composite in which a catalyst component for carbon dioxide hydrogenation is carried in a support including a ceria component exhibiting RWGS reaction activity.

However, in the generation of hydrocarbons by hydrogenating CO2, a technology for a bifunctional catalyst that is capable of simultaneously improving the activities for a reverse water gas shift reaction and a Fischer-Tropsch reaction is insufficient, so there is a need to develop a catalyst having better activity.

DISCLOSURE

Technical Problem

Accordingly, the present disclosure has been made keeping in mind the above problems occurring in the prior art, and a main objective of the present disclosure is to provide a bifunctional catalyst and a method of manufacturing a hydrocarbon using the same to simultaneously cause a reverse water gas shift reaction and a Fischer-Tropsch reaction.

Technical Solution

In order to accomplish the above objective, an embodiment of the present disclosure provides a bifunctional catalyst for manufacturing a hydrocarbon from carbon dioxide and hydrogen. The bifunctional catalyst includes a carbon composite support including cobalt (Co) and nitrogen (N) atoms forming a coordinate bond with the cobalt, and metal particles which exhibit a catalytic activity for a Fischer-Tropsch synthesis reaction and which are dispersed on an inner pore surface and/or an outer surface of the carbon composite support, thus simultaneously promoting a reverse water gas shift reaction and the Fischer-Tropsch synthesis reaction.

In a preferred embodiment of the present disclosure, the carbon composite support may include a structure represented by the following Structural Formula 1.

[Structural Formula 1]

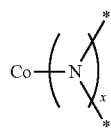

(In Structural Formula 1, x is any one integer of 1 to 4, and '-*' is a site connected to a carbon (C) atom in the carbon composite support)

In a preferred embodiment of the present disclosure, a metal of the metal particles may be one or more selected from the group consisting of iron (Fe), cobalt (Co), copper (Cu), manganese (Mn), nickel (Ni), and zinc (Zn).

In a preferred embodiment of the present disclosure, the metal particles may be used together with one or more enhancers selected from the group consisting of aluminum, potassium, and sodium.

The present disclosure provides a method of manufacturing a bifunctional catalyst for manufacturing a hydrocarbon from carbon dioxide and hydrogen. The method includes (a) forming a mixture of a cobalt precursor including cobalt (Co), nitrogen (N) atoms forming a coordinate bond with the cobalt, and carbon (C) atoms forming a covalent bond with the nitrogen atoms, and a porous silica template, (b) pyrolyzing the mixture, (c) removing the silica template through acid treatment of the pyrolyzed mixture to manufacture a porous carbon composite support, and (d) carrying a precursor of metal particles having a catalytic activity for the Fischer-Tropsch reaction in the porous carbon composite support in step (c).

In a preferred embodiment of the manufacturing method of the present disclosure, the cobalt precursor may include a structure represented by the following Structural Formula 1.

[Structural Formula 1]

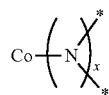

(In Structural Formula 1, x is any one integer of 1 to 4, and '-*' is a site connected to the carbon (C) atom in the cobalt precursor)

In a preferred embodiment of the manufacturing method of the present disclosure, in step (a), the cobalt precursor may be one or more selected from among Co-TMPP, CoTPP, CoAC, and CoPC.

In a preferred embodiment of the manufacturing method of the present disclosure, in step (d), a metal of the metal particles may be one or more selected from the group consisting of cobalt (Co), copper (Cu), manganese (Mn), nickel (Ni), and zinc (Zn).

Another embodiment of a manufacturing method of the present disclosure provides a method of manufacturing a bifunctional catalyst for manufacturing a hydrocarbon from carbon dioxide and hydrogen. The method includes (a) forming a mixture including a cobalt (Co) precursor and an organic compound containing nitrogen (N), (b) pyrolyzing the mixture of step (a) in one or more gas atmospheres selected from the group consisting of gases having nitrogen as an element, including nitrogen, ammonia, or acetonitrile, inert gases including helium or argon, and hydrogen, (c) an acid washing step of washing the pyrolyzed mixture with an acid, and (d) carrying a precursor of metal particles having a catalytic activity for the Fischer-Tropsch reaction in a porous carbon composite support obtained in step (c).

In another embodiment of the manufacturing method of the present disclosure, a carbon source may be further added in the step (a) to form a mixture, and a porous silica template may be further added in the step (a) to form a mixture. When the silica template is further added, the step (c) may be a step of removing the silica template through acid treatment of the pyrolyzed mixture.

In a preferred embodiment of the method of manufacturing the bifunctional catalyst according to the present disclosure, in the step (a), the organic compound containing nitrogen (N) may be one or more selected from among N-methylpyrrole, polyacrylonitrile, 2,5-dimethylpyrrole, maleimide, imidazole, ethylenediamine (EDA), and thiurea.

Another embodiment of the present disclosure provides a method of manufacturing a hydrocarbon from carbon dioxide and hydrogen, the method including reacting the hydrogen and the carbon dioxide in the presence of the catalyst as described above or in the presence of the catalyst manufactured by the method of manufacturing the catalyst.

In a preferred embodiment of the present disclosure, a reaction of the hydrogen and the carbon dioxide may be performed at a temperature of 200 to 450° C. under a pressure within a range of from the atmospheric pressure to 30 atm.

Advantageous Effects

According to the present disclosure, a bifunctional catalyst, which includes a carbon composite support containing cobalt (Co) and a nitrogen (N) atom forming a coordinate bond with the cobalt used as a catalyst support and also includes metal particles having an activity for a Fischer-Tropsch reaction introduced to the surface of the support, has the activity of simultaneously performing a reverse water gas shift reaction and a Fischer-Tropsch reaction. Thereby, it is possible to easily perform hydrogenation of carbon dioxide through a single step.

BEST MODE

Unless defined otherwise, all technical and scientific terms used in the present specification have the same meaning as commonly understood by one of ordinary skill in the art to which this disclosure belongs. In general, the nomenclature used in the present specification is well known and commonly used in the art.

Throughout this specification, when a part is said to "include" a certain component, it means that other components may be further included, rather than excluding other components, unless otherwise stated.

An aspect of the present disclosure relates to a bifunctional catalyst for manufacturing a hydrocarbon from carbon dioxide and hydrogen. The bifunctional catalyst includes a carbon composite support including cobalt (Co) and nitrogen (N) atoms forming a coordinate bond with the cobalt, and metal particles which exhibit a catalytic activity for a Fischer-Tropsch synthesis reaction and which are dispersed on an inner pore surface and/or an outer surface of the carbon composite support, thus simultaneously promoting a reverse water gas shift reaction and the Fischer-Tropsch synthesis reaction.

Figure 1:
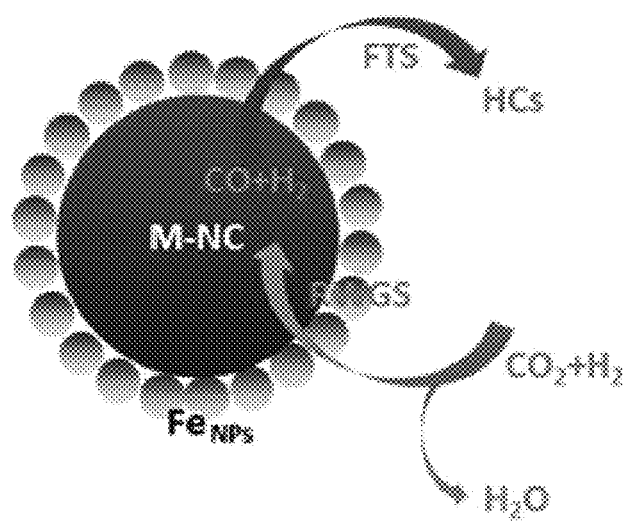
FIG. 1 shows a schematic view in which a reverse water gas shift reaction and a Fischer-Tropsch reaction occur over a catalyst for carbon dioxide reduction according to the present disclosure.
Figure 2:
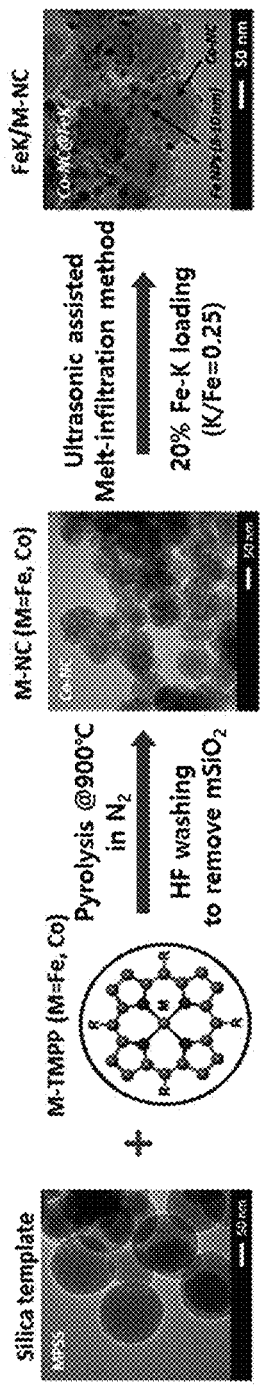
FIG. 2 is a schematic view showing a process of manufacturing a catalyst for carbon dioxide reduction according to the present disclosure.
Figure 3:
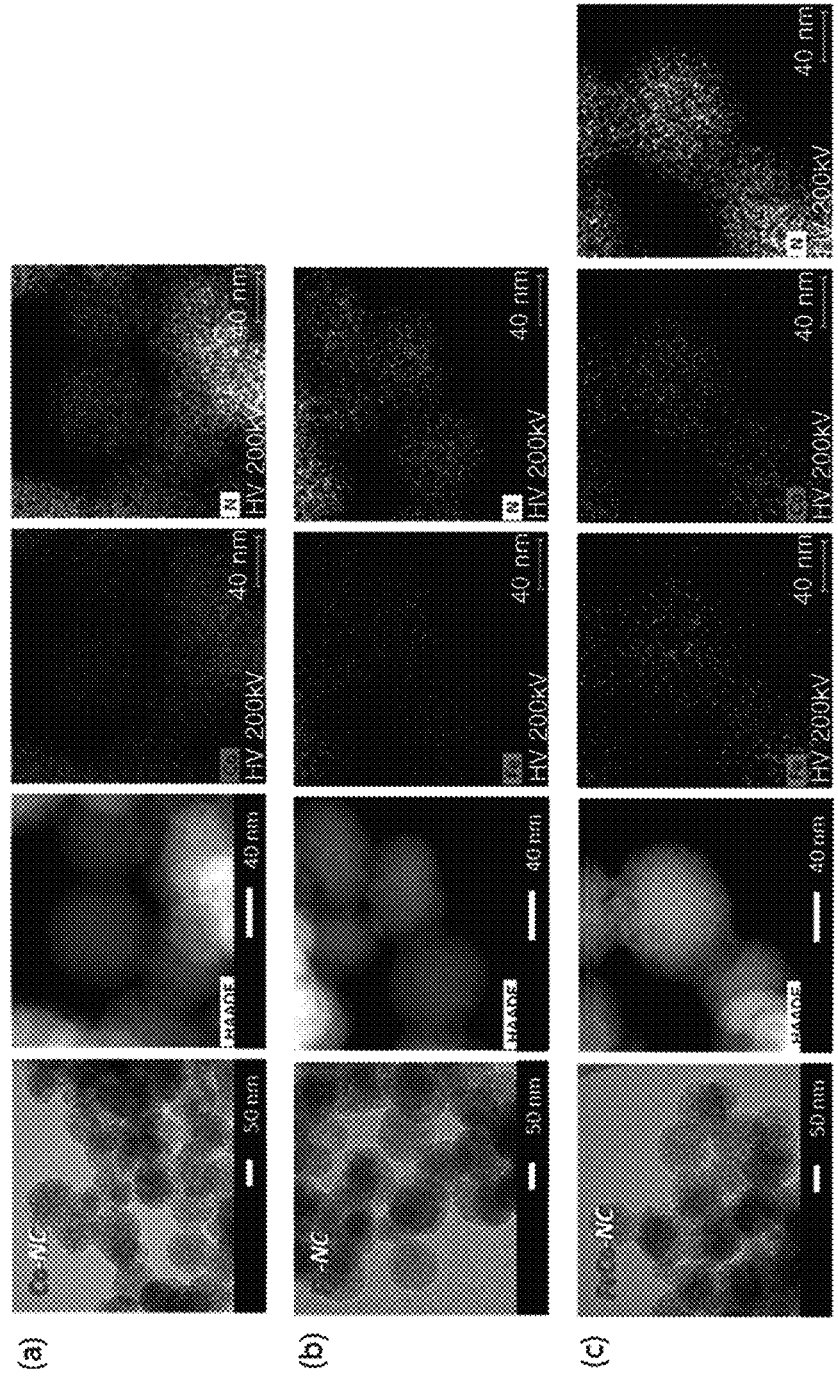
FIG. 3 shows TEM photographs of carbon composite support materials according to (a) a Co—NC carbon composite support, (b) a Fe—NC carbon composite support, and (c) a FeCo—NC carbon composite support.
Figure 4:
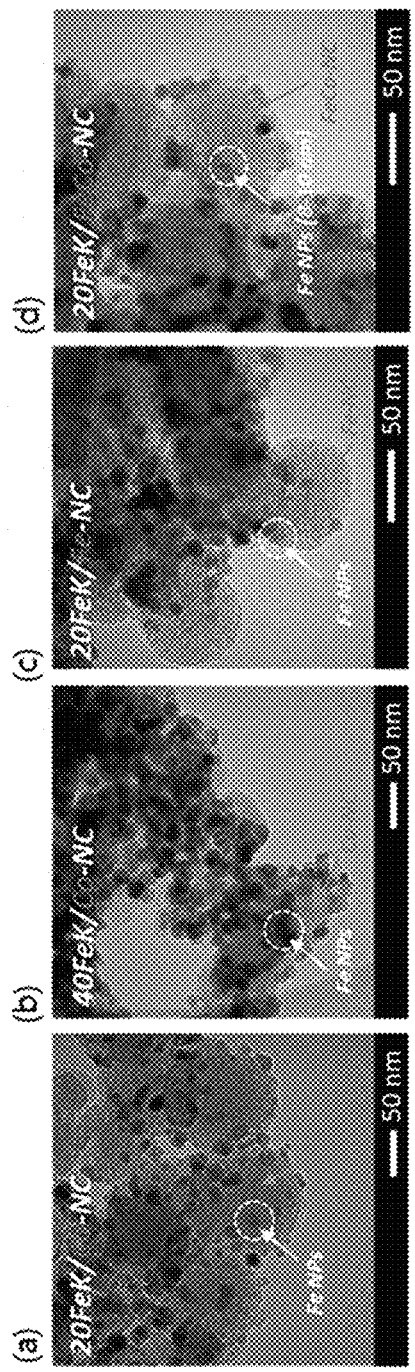
FIG. 4 shows TEM photographs of catalysts according to (a) Example 1, (b) Example 2, (c) Comparative Example 2, and (d) Comparative Example 3.

More specifically, as shown in FIG. 1, the catalyst for a reduction reaction of carbon dioxide according to the present disclosure includes the metal particles exhibiting the activity for the Fischer-Tropsch synthesis reaction (hereinafter, referred to as 'FTS reaction') on a portion of the surface of the carbon composite support, thus simultaneously exhibiting the activity for the reverse water gas shift reaction (hereinafter, referred to as 'RWGS reaction') and the activity for the FTS reaction.

Without being limited by theory, it is expected that the cobalt element coordinated by the nitrogen (N) atom in the carbon composite support acts as an active site in the RWGS reaction. Further, the carbon coordinated with the nitrogen (N) atom may act as an anchoring site with the metal particles, thus helping to effectively introduce the catalyst particles for the FTS reaction, as well as providing a strong electron donating effect from the nitrogen atom, thereby acting as an adsorption and activation site for carbon dioxide ($CO_2$).

The carbon composite support may include a structure represented by the following Structural Formula 1, and the carbon composite support may be manufactured using a compound including the structure represented by the following Structural Formula 1. Examples of the compound including the structure represented by the following Structural Formula 1 include 5,10,15,20-tetrakis(4-methoxyphenyl)-21H,23H-porphine cobalt(II) (Co-TMPP), cobalt(II) tetraphenyl porpyrine (CoTPP), cobalt(II) acetate (CoAc), and cobalt(II) phthalocyanine (CoPc), but are not limited thereto.

[Structural Formula 1]

(In Structural Formula 1, is a site connected to a carbon (C) atom in the carbon composite support)

Further, the carbon composite support may include a structure represented by any one of the following Structural Formula 1-1 to Structural Formula 1-4. The carbon composite support may be manufactured using a compound including a structure represented by any one of the following Structural Formula 1-1 to Structural Formula 1-4.

[Structural Formula 1-1]

[Structural Formula 1-2]

[Structural Formula 1-3]

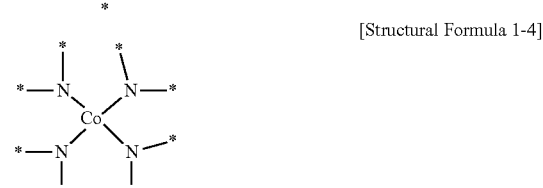

[Structural Formula 1-4]

(In Structural Formula 1-1 to Structural Formula 1-4, '-*' is a site connected to a carbon (C) atom in the carbon composite support)

The metal particles having an activity for the FTS reaction introduced into the carbon composite support include one or more selected from the group consisting of iron (Fe), cobalt (Co), copper (Cu), manganese (Mn), nickel (Ni), and zinc (Zn), without limitation thereto. The metal particles having an activity for the FTS reaction may be used together with one or more enhancers selected from among aluminum, potassium, and sodium.

Further, the metal particles may be included in a content of 1 to 70 wt % based on 100 wt % of the carbon composite support. When the content of the metal particles is within the above numerical range, the RWGS and FTS reactions occur appropriately simultaneously, thereby increasing the reaction activity of directly generating hydrocarbons from $CO_2$.

Further, the present disclosure provides a method of manufacturing a catalyst for a reduction reaction of carbon dioxide. The method includes (a) forming a mixture of a cobalt precursor including cobalt (Co), nitrogen (N) atoms forming a coordinate bond with the cobalt, and carbon (C) atoms forming a covalent bond with the nitrogen atoms, and a porous silica template, (b) pyrolyzing the mixture at 500 to 1000° C., (c) removing the silica template through acid treatment of the pyrolyzed mixture to manufacture a carbon composite support, and (d) dispersing metal particles having a catalytic activity for a Fischer-Tropsch reaction in the carbon composite support to perform bonding. The carbon composite support exhibits the catalytic activity for the reverse water gas shift reaction.

The step (a) is a step of forming a mixture of a cobalt precursor including cobalt (Co), nitrogen (N) atoms forming a coordinate bond with the cobalt, and carbon (C) atoms forming a covalent bond with the nitrogen atoms, and a porous silica template having a regular structure.

The cobalt precursor may include a structure represented by the following Structural Formula 1.

[Structural Formula 1]

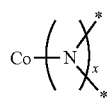

(In Structural Formula 1, x is any one integer of 1 to 4, and '-*' is a site connected to a carbon (C) atom in the cobalt precursor)

Further, the structure represented by the following Structural Formula 1 in the cobalt precursor may be a structure represented by any one of the following Structural Formula 1-1 to Structural Formula 1-4.

[Structural Formula 1-1]

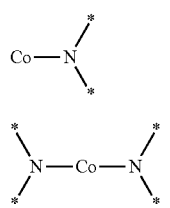

[Structural Formula 1-2]

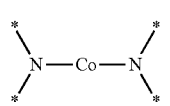

[Structural Formula 1-3]

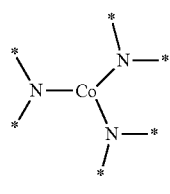

[Structural Formula 1-4]

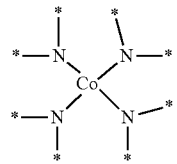

(In Structural Formula 1-1 to Structural Formula 1-4, '-*' is a site connected to a carbon (C) atom in the cobalt precursor)

Further, in the step (a), the cobalt precursor may be one or more selected from among Co-TMPP, CoAc, CoPc, and CoTPP, but is not limited thereto.

Subsequently, the step (b) is a step of pyrolyzing the mixture manufactured in the step (a) at 500 to 1000° C. to form a carbon composite support structure.

For example, when the porous silica template is mixed with a porphyrin precursor (Co-TMPP, 5,10,15,20-tetrakis (4-methoxyphenyl)-21H,23H-porphine cobalt(II) (Co-TMPP)) to be pyrolyzed, a carbon composite support having the pores filled with carbon is formed. The pyrolyzing may be performed in a nitrogen gas atmosphere at 500 to 1000° C. for 1 to 5 hours.

Next, the step (c) is a step of removing the silica template through acid treatment of the pyrolyzed mixture to manufacture the carbon composite support. The carbon composite support from which silica is removed using the acid treatment is washed with distilled water and then dried.

As a solution for the acid treatment, an aqueous HF solution is mainly used, but the solution is not limited as long as the solution is capable of removing silica. Thereafter, the carbon composite support may be washed 1 to times with distilled water. Thereafter, the carbon composite support may be dried in an oven to use.

Subsequently, the step (d) is a step of dispersing the metal particles having the catalytic activity for the Fischer-Tropsch reaction in the carbon composite support to perform bonding.

More specifically, the carrying may be performed using a known general catalyst carrying method. More preferably, iron may be carried in the carbon composite support by using an ultrasonic assisted melt-infiltration method using ultrasonic waves. After the metal precursor is dissolved in an aqueous solution, the carbon composite support is added and sonicated for 20 to 40 minutes, and then dried in an oven at a temperature of 80 to 110° C. for 20 to 24 hours.

In the step (d), the metal of the metal particles contains one or more selected from the group consisting of iron (Fe), cobalt (Co), copper (Cu), manganese (Mn), nickel (Ni), and zinc (Zn), but is not limited thereto. The metal particles having an activity for the FTS reaction may be used together with one or more enhancers selected from among aluminum, potassium, and sodium.

When the metal is iron, as a compound used as the iron precursor, for example, iron nitrate hydrate (Fe $(NO_3)_3 \cdot 9H_2O$), iron acetate ($Fe(CO_2CH_3)_2$), iron oxalate hydrate ($Fe(C_2O_4)_3 \cdot 6H_2O$), iron acetylacetate ($Fe(C_5H_7O_2)_3$), or iron chloride ($FeCl_3$) may be used.

Further, it is preferable that the metal particles be included in a content of 1 to 70 wt % based on 100 wt % of the carbon composite support.

As such, in the present disclosure, a porous or mesoporous silica template and a porphyrin precursor may be mixed and pyrolyzed, thus manufacturing the carbon composite support and also manufacturing a hybrid catalyst in which the nanoparticles exhibiting the catalytic activity for the Fischer-Tropsch reaction are bonded to carbon composite support.

Further, in the present disclosure, when the cobalt precursor is a compound that is not represented by Structural Formula 1, the cobalt precursor may be treated with a nitrogen source, thus inducing conversion into Structural Formula 1.

There is provided a method of manufacturing a bifunctional catalyst for manufacturing a hydrocarbon from carbon dioxide and hydrogen to simultaneously promote a reverse water gas shift reaction and a Fischer-Tropsch synthesis reaction. The method includes (a) forming a mixture including a cobalt (Co) precursor and an organic compound containing nitrogen (N), (b) pyrolyzing the mixture of the step (a) in one or more gas atmospheres selected from the group consisting of gases having nitrogen as an element, including nitrogen, ammonia, or acetonitrile, inert gases including helium or argon, and hydrogen, (c) washing the pyrolyzed mixture with an acid, and (d) carrying a precursor of metal particles having a catalytic activity for the Fischer-Tropsch reaction in a porous carbon composite support obtained in step (c).

The cobalt precursor of the step (a) is a compound of cobalt, which does not correspond to Structural Formula 1. Non-limiting examples of the precursor may include $Co(NO_3)_2$, $CoSO_4$, and $CoCl_2$. Further, the organic compound containing nitrogen (N) in the step (a) is preferably one or more selected from among N-methylpyrrole, polyacrylonitrile, 2,5-dimethylpyrrole, maleimide, imidazole, ethylenediamine (EDA), and thiurea, but is not limited thereto. Further, in the step (a), a carbon source and/or a porous silica template may be further mixed to form a mixture. The carbon source is not limited as long as the carbon source is capable of generating carbon using pyrolyzing, and may be, for example, carbon black.

Subsequently, the step (b) is a step of pyrolyzing the mixture of the step (a), and the carbon composite support in which cobalt metal is bonded to carbon and which is represented by Structural Formula 1 is formed using the pyrolyzing. The pyrolyzing may be performed in the range of 400 to 1000° C.

Next, the step (c) is an acid washing process of performing washing with an acid in order to remove cobalt particles or impurities that are separated and then pushed out to the surface in the pyrolyzing step. In the pyrolyzing process of the step (b), nitrogen forms a coordinate bond with cobalt particles and is bonded to carbon to achieve a process in which cobalt is fixed to a carbon body. However, some cobalt particles may be separated without the above-mentioned process and then pushed out to the surface of the carbon body. The pushed impurities such as cobalt metal and separated debris are removed through the acid washing process. After the acid washing, the carbon composite support may be washed 1 to 3 times with distilled water, and then the porous carbon composite support may be dried in an oven to use.

When the silica template is included in the step (a), the step of performing washing with an acid in the step (c) is replaced by a step of removing the added silica template with an acid. In this way, in the process of removing the silica template with the acid, the cobalt nanoparticles or impurities pushed out during the pyrolyzing process may be removed together. Thereafter, a washing step using distilled water may be performed as before.

Subsequently, the step (d) is a step in which metal particles exhibiting the catalytic activity for the Fischer-Tropsch reaction are dispersed in the carbon composite support to perform bonding, and a general catalyst carrying method is the same as described above.

The metal particles exhibiting the catalytic activity for the Fischer-Tropsch reaction include one or more selected from the group consisting of iron (Fe), cobalt (Co), copper (Cu), manganese (Mn), nickel (Ni), and zinc (Zn), without limitation thereto. The metal particles having the activity for the FTS reaction may be used together with one or more enhancers selected from among aluminum, potassium, and sodium.

It is preferable that the metal particles be included in a content of 1 to 70 wt % based on 100 wt % of the carbon composite support.

As such, in the present disclosure, a porous, that is, mesoporous silica template and the organo-metal precursor according to the present disclosure may be mixed and pyrolyzed, thus manufacturing the carbon composite support and also manufacturing a hybrid catalyst in which the nanoparticles exhibiting the catalytic activity for the Fischer-Tropsch reaction are bonded to carbon composite support.

Further, the present disclosure provides a method of manufacturing a hydrocarbon product from a reduction reaction of carbon dioxide, in which a Fischer-Tropsch reaction and a reverse water gas shift reaction are simultaneously performed in the presence of the catalyst for the reduction reaction of carbon dioxide manufactured according to the manufacturing method.

The catalyst for the reduction reaction of carbon dioxide manufactured according to the manufacturing method is used for the reaction after reduction in a hydrogen atmosphere in the region of 200 to 700° C. The reduction reaction of reacting a mixed gas containing carbon dioxide and hydrogen to thus manufacture a liquid hydrocarbon is performed under a reaction condition similar to that of the Fischer-Tropsch synthesis reaction. Accordingly, the reduction reaction is preferably performed at a reaction temperature of 200 to 450° C. under a pressure of normal pressure to 30 atm.

In the reduction reaction of carbon dioxide, when the reaction temperature is lower than 200° C., the reaction speed is not sufficient. When the reaction temperature is higher than 450° C., more by-products may be generated.

Further, when the reaction pressure in the reduction reaction of carbon dioxide is lower than the normal pressure, the conversion rate of carbon dioxide by the reaction is not high. Further, when the reaction pressure is higher than 30 atm, the economic efficiency of the process is deteriorated.

Further, in the reduction reaction of carbon dioxide, the space velocity of the reactant is preferably 500 to 10000 $ml/gcath^{-1}$, but is not limited thereto.

Mode for Disclosure

Hereinafter, a catalyst for a reduction reaction of carbon dioxide according to the present disclosure will be described in detail through Examples and Experimental Examples.

When it is judged that a detailed description of a related known function or configuration may unnecessarily obscure the gist of the present disclosure in describing in detail the principle of the preferred embodiment of the present disclosure, the detailed description thereof will be omitted.

Examples 1 and 2 and Comparative Examples 1 to 3

Example 1: 20FeK/Co—NC (a) Synthesis of Carbon Composite Support

First, a porous silica (OMS, spherical shape) having regular pores (particle diameter of 20 nm) was mixed with a porphyrin precursor. As the precursor, 5,10,15,20-tetrakis (4-methoxyphenyl)-21H,23H-porphine cobalt(II) (Co-TMPP) was used. Next, the mixture was pyrolyzed in a nitrogen gas atmosphere at 800° C. for 3 hours. A carbon composite support which was pyrolyzed and on which metal particles were formed was washed with a 10% HF aqueous solution to thus remove Co nanoparticles and silica present on the surface thereof. Next, the resultant material was washed three times with distilled water and then dried at 80° C. for 24 hours to obtain a carbon composite support (Co—NC).

(b) Carrying of Iron Nanoparticles

Next, in order to carry iron, which is a catalytically active component, after 1.85 g of an iron precursor was dissolved in 40 ml of ethanol, 1 g of the carbon composite support was added thereto, followed by sonication for 30 minutes and then drying in an oven at 100° C. for 24 hours. The dried resultant material was calcined with nitrogen at 450° C. for 3 hours to finally manufacture a catalyst impregnated with iron in carbon nitride.

(c) Carrying of Potassium

Next, in order to carry potassium in a Fe/Co—NC catalyst, a potassium precursor ($K_2CO_3$) was dissolved in an amount selected from the range of a K/Fe weight ratio of 0.1 to 0.25 in distilled water, impregnated in the Fe/Co—NC catalyst, and dried in an oven at 100° C. for 24 hours. The dried resultant material was calcined with nitrogen at 500° C. for 3 hours to finally manufacture a FeK/Co—NC catalyst.

Example 2: 40FeK/Co—NC

A 40FeK/Co—NC catalyst was manufactured using the same condition as in Example 1, except that Fe was carried in an amount of 40 wt % based on the carbon composite support in the (b) step of carrying the iron nanoparticles in Example 1.

Comparative Example 1: 20FeK/C

A 20FeK/C catalyst was manufactured using activated carbon as a support instead of the carbon composite support without the (a) step of synthesizing the carbon composite support of Example 1.

Comparative Example 2: 20FeK/Fe—NC

A 20FeK/Fe—NC catalyst was manufactured using the same condition as in Example 1, except that 5,10,15,20-tetrakis(4-methoxyphenyl)-21H,23H-porphine iron(III) chloride (Fe-TMPPCl) was used instead of Co-TMPP as a precursor of the carbon composite support in the (a) synthesis of the carbon composite support of Example 1.

Comparative Example 3: 20FeK/FeCo—NC

A 20FeK/FeCo—NC catalyst was manufactured using the same condition as in Example 1, except that Fe-TMPPCl was further added together with Co-TMPP as a precursor of the carbon composite support in the (a) synthesis of the carbon composite support of Example 1.

Experimental Example: Reduction Reaction of Carbon Dioxide

Experimental Example 1: Simultaneous Reaction of RWGS and FTS

A RWGS reaction and a FT reaction were simultaneously performed using a fixed-bed tubular reactor (fixed-bed reactor, stainless steel material, and diameter of ⅜ inch). In order to measure and adjust a reaction temperature, a thermocouple was provided in a reaction tube to adjust the temperature during the reaction. For the reaction, first, quartz wool was placed under a catalyst in the reaction tube, and 0.3 g of the catalysts obtained in Comparative Examples 1 to 3 and Examples 1 and 2 were loaded thereon. Before the reaction, a reduction reaction was performed at 350° C. for 5 hours at a molar ratio of hydrogen to carbon monoxide (CO) of 2:1.

The reaction was performed at 300° C. at a molar ratio of hydrogen to carbon dioxide ($CO_2$) of 3:1 in practice. The actual flow rate of hydrogen and carbon dioxide under the pressure condition of 25 bar was 2000 $mL \cdot g_{cat}^{-1} \cdot h^{-1}$ in terms of a GHSV value. During the reaction process for a total of 69 hours, the reactants and products were analyzed through gas chromatography (GC), and water incidentally generated after the reaction was recovered in a cooling trap.

Flow rate analysis before and after the reaction was accurately performed using a wet gas meter device in real time. Accordingly, the conversion rate of carbon dioxide ($CO_2$) for the reaction for 69 hours was calculated according to the following Mathematical Equation 1, and is shown in FIG. 5 below.

[Mathematical Equation 1]

$$CO_2 \text{conversion}(\%) = \frac{CO_2 \text{mol before reaction} - CO_2 \text{mol after reaction}}{CO_2 \text{mol before reaction}} \times 100(\%)$$

Figure 5:
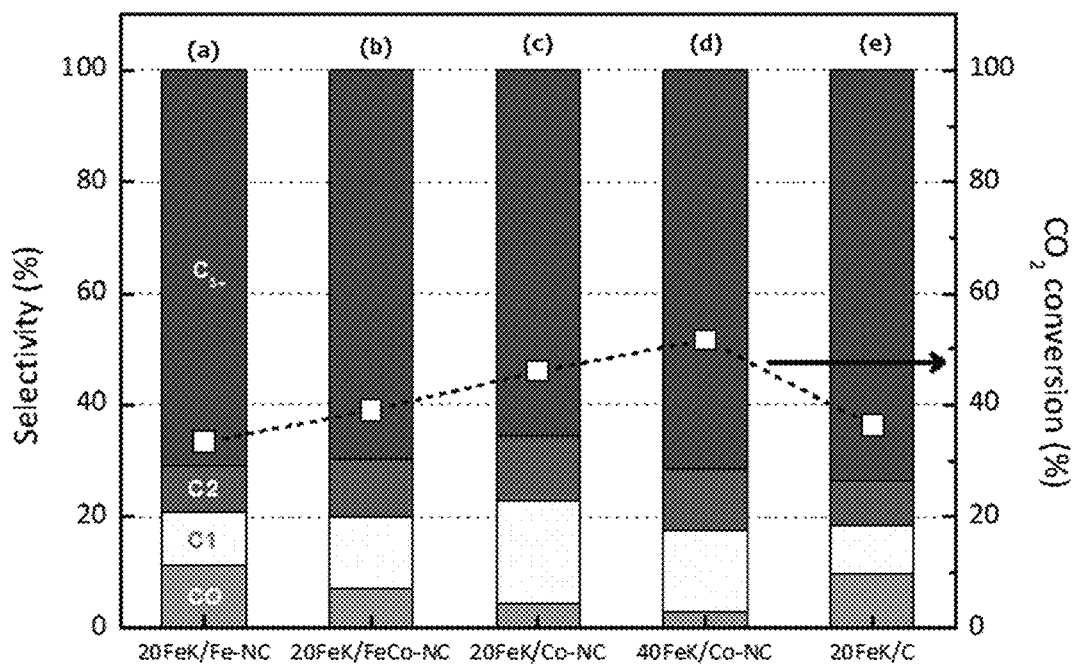
FIG. 5 shows the conversion rate of carbon dioxide and the selectivity of a hydrocarbon in a conversion reaction of carbon dioxide using individual catalysts according to (a) Comparative Example 2, (b) Comparative Example 3, (c) Example 1, (d) Example 2, and (e) Comparative Example 1.

As shown in FIG. 5, in the conversion reaction of carbon dioxide over the catalyst manufactured according to Example 2, the conversion rate of carbon dioxide was the highest 51.7%, and the conversion rate of carbon dioxide over the catalyst according to Comparative Example 2 was measured to be the lowest 33.4%. Further, the proportion of hydrocarbons having carbon atoms of 3 or more in the product obtained according to the conversion reaction of carbon dioxide over each catalyst was calculated, and as a result, the proportion was found to be 71.6% when the catalyst manufactured according to Example 2 was used.

INDUSTRIAL APPLICABILITY

As described above, the present disclosure has been described with reference to the accompanying drawings and embodiments, which are merely exemplary, and those of ordinary skill in the art will understand that various modifications and equivalent other embodiments are possible therefrom. Therefore, the technical protection scope of the present disclosure should be defined by the following claims.

The invention claimed is:

1. A bifunctional catalyst for manufacturing a hydrocarbon from carbon dioxide and hydrogen, the bifunctional catalyst comprising:
   a carbon composite support including cobalt (Co) and nitrogen (N) atoms forming a coordinate bond with the cobalt; and
   metal particles which exhibit a catalytic activity for a Fischer-Tropsch synthesis reaction and which are dispersed on an inner pore surface and/or an outer surface of the carbon composite support, thus simultaneously promoting a reverse water gas shift reaction and the Fischer-Tropsch synthesis reaction, wherein the carbon composite support includes a structure represented by a following Structural Formula 1:

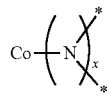

[Structural Formula 1]

in the Structural Formula 1, x is any one integer of 1 to 4, and '-*' is a site connected to a carbon (C) atom in the carbon composite support.

2. The bifunctional catalyst of claim 1, wherein a metal of the metal particles is one or more selected from the group consisting of iron (Fe), cobalt (Co), copper (Cu), manganese (Mn), nickel (Ni), and zinc (Zn).

3. The bifunctional catalyst of claim 2, wherein the metal particles are used together with one or more enhancers selected from the group consisting of aluminum, potassium, and sodium.

4. A method of manufacturing a hydrocarbon from carbon dioxide and hydrogen, the method comprising:
reacting the hydrogen and the carbon dioxide in a presence of the catalyst described in claim 1.

5. The method of claim 4, wherein a reduction reaction of the carbon dioxide is performed at a reaction temperature of 200 to 450° C. under a pressure of normal pressure to 30 atm.

6. A method of manufacturing a bifunctional catalyst for manufacturing a hydrocarbon from carbon dioxide and hydrogen to simultaneously promote a reverse water gas shift reaction and a Fischer-Tropsch synthesis reaction, the method comprising:
(a) forming a mixture of a cobalt precursor including cobalt (Co), nitrogen (N) atoms forming a coordinate bond with the cobalt, and carbon (C) atoms forming a covalent bond with the nitrogen atoms, and a porous silica template;
(b) pyrolyzing the mixture;
(c) removing the silica template through acid treatment of the pyrolyzed mixture to manufacture a porous carbon composite support; and
(d) carrying a precursor of metal particles having a catalytic activity for the Fischer-Tropsch reaction in the porous carbon composite support in step (c).

7. The method of claim 6, wherein the cobalt precursor includes a structure represented by a following Structural Formula 1:

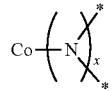

[Structural Formula 1]

(in the Structural Formula 1, x is any one integer of 1 to 4, and '-*' is a site connected to the carbon (C) atom in the cobalt precursor).

8. The method of claim 6, wherein in step (a), the precursor including a cobalt metal, nitrogen, and carbon is one or more selected from the group consisting of Co-TMPP, CoTPP, CoAC, and CoPC.

9. A method of manufacturing a hydrocarbon from carbon dioxide and hydrogen, the method comprising:
reacting the hydrogen and the carbon dioxide in a presence of the catalyst manufactured by the manufacturing method according to claim 5.

10. The method of claim 9, wherein a reduction reaction of the carbon dioxide is performed at a reaction temperature of 200 to 450° C. under a pressure of normal pressure to 30 atm.

11. A method of manufacturing a bifunctional catalyst for manufacturing a hydrocarbon from carbon dioxide and hydrogen to simultaneously promote a reverse water gas shift reaction and a Fischer-Tropsch synthesis reaction, the method comprising:
(a) forming a mixture including a cobalt (Co) precursor and an organic compound containing nitrogen (N);
(b) pyrolyzing the mixture of step (a) in one or more gas atmospheres selected from the group consisting of gases having nitrogen as an element, including nitrogen, ammonia, or acetonitrile, inert gases including helium or argon, and hydrogen;
(c) an acid washing step of washing the pyrolyzed mixture with an acid; and
(d) carrying a precursor of metal particles having a catalytic activity for the Fischer-Tropsch reaction in a porous carbon composite support obtained in step (c),
wherein a porous silica template is further added in the step (a) to form a mixture, and the step (c) is a step of removing the silica template through acid treatment of the pyrolyzed mixture.

12. The method of claim 11, wherein a carbon source is further added in the step (a) to form a mixture.

\* \* \* \* \*